United States Patent

François et al.

Patent Number: 5,081,120
Date of Patent: Jan. 14, 1992

[54] 2-,21-DINOREBURNAMENINES CONTAINING A 15-AMINATED GROUP

[75] Inventors: Clémence François, Paris; Jean L. Haesslein, Rosny-sout-Bois; Francis Petit, Bondy; Mauricette Degryse, Bagnolet, all of France

[73] Assignee: Roussel Uclaf, Romainville, France

[21] Appl. No.: 460,965

[22] PCT Filed: Jun. 28, 1989

[86] PCT No.: PCT/FR89/00335
§ 371 Date: Feb. 23, 1990
§ 102(e) Date: Feb. 23, 1990

[87] PCT Pub. No.: WO90/00171
PCT Pub. Date: Jan. 11, 1990

[30] Foreign Application Priority Data

Jun. 28, 1988 [FR] France .................................. 88 08648

[51] Int. Cl.$^5$ ................... A61K 31/535; A61K 31/41; C07D 413/00; C07D 471/00
[52] U.S. Cl. ................................ 514/233.2; 514/255; 514/283; 544/125; 544/361; 546/51
[58] Field of Search ............... 546/51; 514/283, 233.2, 514/255; 544/125, 361

[56] References Cited

U.S. PATENT DOCUMENTS 4,123,535 10/1978 Pfaffli .................................. 424/256

OTHER PUBLICATIONS

Szantay, Csaba et al., Chemical Abstract 100(25) 210, 238t and copy of CAS on line structure, Abstract of DE 3323606 A1 12 Jan. 84.

*Primary Examiner*—Mukund J. Shah
*Assistant Examiner*—Matthew V. Grumbling
*Attorney, Agent, or Firm*—Bierman and Muserlian

[57] ABSTRACT

A compound selected from the group consisting of a compound of the formula (I):

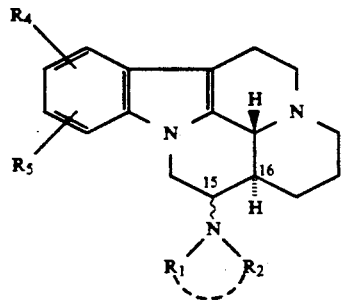

in which $R_1$ and $R_2$ are individually selected from the group consisting of hydrogen, an alkyl of 1 to 5 carbon atoms, —$(CH_2)_n$—OH in which n is between 2 and 5, an aryl or arylalkyl of 7 to 12 carbon atoms, these two radicals being optionally substituted, $$-\underset{\underset{O}{\|}}{C}-R_3$$

in which $R_3$ is an alkyl of 7 to 12 carbon atoms, these two radicals being optionally substituted, with the proviso that $R_1$ and $R_2$ are not both aryl simultaneously, or $R_1$ and $R_2$ form, together with the nitrogen atom to which they are linked, a saturated or unsaturated heterocyclic which can contain a second heteroatom chosen from oxygen, sulphur and nitrogen optionally substituted by an alkyl of 1 to 5 carbon atoms, aryl, arylalkyl of 7 to 12 carbon atoms, these radicals being optionally substituted, $R_4$ and $R_5$ are individually selected from the group consisting of hydrogen, halogen, alkyl or alkoxy of 1 to 5 carbon atoms, hydroxy, trifluoromethyl or nitro, the said products of formula (I) being in all the possible enantiomeric and diastereoisomeric forms and its non-toxic, pharmaceutically acceptable acid addition salts having an excellent analgesic activity.

11 Claims, No Drawings

2-,21-DINOREBURNAMENINES CONTAINING A 15-AMINATED GROUP

The invention relates to new derivatives of 20,21-dinoreburnamenine substituted at position 15 by an aminated group, and their salts, their preparation process and the intermediates thus obtained, their use as medicaments and the pharmaceutical compositions containing them.

The invention relates to new compounds of formula (I):

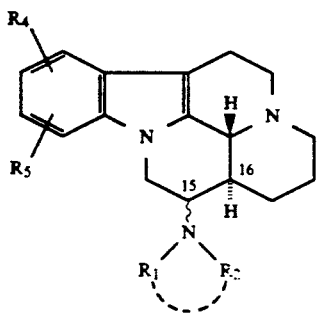

in which $R_1$ and $R_2$, ident different, represent a hydrogen atom, an alkyl radical containing 1 to 5 carbon atoms, a —$(CH_2)n$—OH radical, in which n is between 2 and 5, an aryl or arylalkyl radical containing 7 to 12 carbon atoms, these two radicals being optionally substituted, a

radical in which $R_3$ is an alkyl radical containing 1 to 5 carbon atoms, an aryl or arylalkyl radical containing 7 to 12 carbon atoms, these two radicals being optionally substituted, $R_1$ and $R_2$, however, not being able to represent an aryl radical simultaneously, or $R_1$ and $R_2$ form, together with the nitrogen atom to which they are linked, a saturated or unsaturated heterocyclic radical which can contain a second heteroatom chosen from oxygen, sulphur and nitrogen atoms, this latter being optionally substituted by an alkyl radical containing 1 to 5 carbon atoms, an aryl radical, an arylalkyl radical containing 7 to 12 carbon atoms, these radicals being optionally substituted, $R_4$ and $R_5$, identical or different, represent a hydrogen atom, a halogen atom, an alkyl or alkoxy radical containing 1 to 5 carbon atoms, a hydroxy, trifluoromethyl or nitro radical, the said products of formula (I) being in all the possible enantiomeric and diastereoisomeric forms and in the form of addition salts with acids.

The term alkyl radical preferably represents a methyl, ethyl, n-propyl or isopropyl radical, but also an n-butyl, isobutyl or n-pentyl radical. The term aryl radical preferably means a phenyl or naphthyl radical and the term arylalkyl radical containing 7 to 12 carbon atoms preferably means a benzyl or phenethyl radical. The aryl and aryl-alkyl radicals are optionally substituted by 1, 2 or 3 radicals chosen from the group formed by halogen atoms, and the following radicals: methyl, ethyl, methoxy, ethoxy, trifluoromethyl, amino and nitro.

When $R_1$ and $R_2$ form, together with the nitrogen atom, a heterocycle, it is preferably, for example, one of the following cycles: pyrrolidino, piperidino, morpholino, piperazinyl, methylpiperazinyl, ethylpiperazinyl, propylpiperazinyl, phenylpiperazinyl, or benzylpiperazinyl, when $R_1$ and $R_2$ represent these last two radicals, the phenyl and benzyl radicals can be optionally substituted by the substituents already mentioned previously.

When $R_4$ and $R_5$ represent an alkoxy radical, it is preferably a methoxy or ethoxy radical, but they can also represent a propoxy, an isopropoxy, or a linear, secondary or tertiary butoxy radical.

When $R_4$ and $R_5$ represent an alkyl radical, it is preferably a methyl radical; it can also be an ethyl, propyl, isopropyl, or linear or branched butyl radical.

When $R_4$ and $R_5$ represent a halogen atom, it is preferred to be a chlorine atom, but they can also represent a fluorine, bromine or iodine atom.

In the products of formula (I), the hydrogen atom in position 3 and the hydrogen atom in position 16 can each occupy one or other of the alpha or beta orientations, which determines the existence of cis and trans diastereoisomers. Furthermore, the nitrogen atom linked to the carbon in position 15 can be in alpha or beta form.

The invention relates in particular to the compounds of formula (I) characterized in that $R_1$ and $R_2$, identical or different, represent a hydrogen atom, a methyl or ethyl radical, a

radical in which $R_3$ is a methyl, ethyl, phenyl or benzyl radical optionally substituted by one or more chlorine atoms, or a —$CH_2$—$CH_2$—OH radical, or $R_1$ and $R_2$ form, together with the nitrogen atom, a pyrrolidinyl, morpholinyl or piperazinyl radical, the nitrogen atom of which is substituted by a methyl or phenyl radical, and the compounds of formula (I) characterized in that $R_4$ and $R_5$ represent a hydrogen atom or $R_4$ represents a nitro radical in position 9 or 11 and $R_5$ represents a hydrogen atom, as well as their addition salts with acids.

The invention relates especially to the products in which $R_4$ and $R_5$ each represent a hydrogen atom.

Quite particularly a subject of the invention is the products described hereafter and especially:

[(±)    (15-alpha,16-alpha)]-14,15-dihydro-N-methyl-20,21-dinoreburnamenin-15-amine,

[(±)    (15-alpha,16-alpha)]-14,15-dihydro-20,21-dinoreburnamenin-15-amine,

[(±)    (15-alpha,16-alpha)]-2-[(14,15-dihydro-20,21-dinoreburnamenin-15-yl)-methylamino]-ethanol, as well as their addition salts with acids.

The addition salts with mineral or organic acids of the products of formula (I) can be, for example, the salts formed with the following acids: hydrochloric, hydrobromic, hydroiodic, nitric, sulphuric, phosphoric, propionic, acetic, formic, benzoic, maleic, fumaric, succinic, tartaric, citric, oxalic, glyoxylic, aspartic, ascorbic, alkylmonosulphonic such as methanesulphonic, ethanesulphonic and propanesulphonic, alkyldisulphonic such as methanedisulphonic and alpha,beta-ethanedisulphonic, arylmonosulphonic such as benzenesulphonic, and aryldisulphonic.

Also a subject of the invention is a process for the preparation of compounds of formula (I), ad defined previously, characterized in that a compound of formula (II):

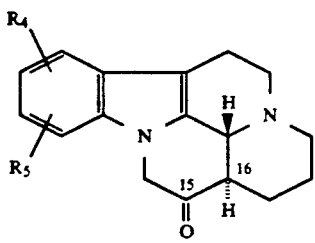

in which $R_4$ and $R_5$ have the previously indicated meaning, is subjected
either to the action of an aliphatic amine of formula $(III_A)$:

   $(III_A)$ in which $R'_1$ has the previous meaning of $R_1$, except for hydrogen, so as to obtain a compound of formula (IV):

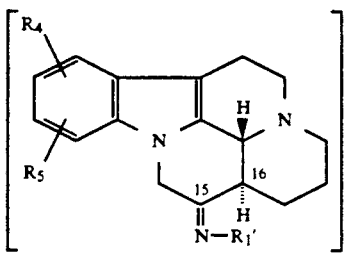

which is reduced so as to obtain a compound of formula $(I_{A1})$:

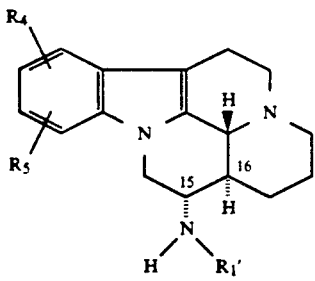

in which $R'_1$, $R_3$ and $R_4$ have the meaning already indicated,
or to the action of a heterocyclic amine of formula $(III_B)$:

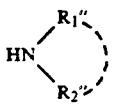   $(III_B)$ in which $R''_1$ and $R''_2$ form, together with the nitrogen atom to which they are linked, the same heterocyclic amines as those given previously for $R_1$ and $R_2$, so as to obtain a compound of formula (V):

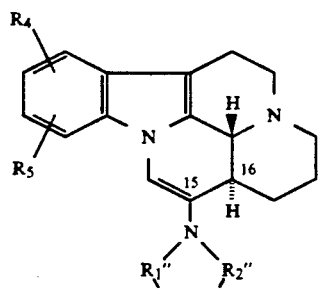

which is reduced so as to obtain a compound of formula $(I_{A2})$:

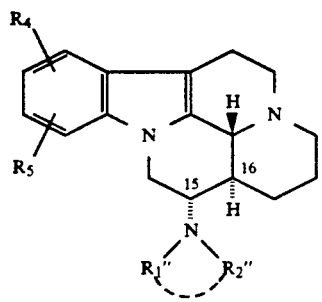

in which $R''_1$, $R''_2$, $R_4$ and $R_5$ have the values previously given
or to the action of a reducing agent so as to obtain a compound of formula (VI):

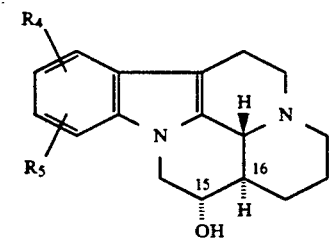

the hydroxyl function of which is activated and it is subjected
either to the action of an aliphatic amine $(III_A)$:

H$_2$N—R'$_1$   $(III_A)$

R'$_1$ having the previous meaning, so as to obtain a compound of formula $(I_{B1})$:

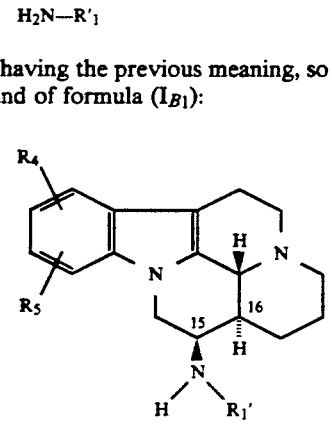

R'$_1$, R$_4$ and R$_5$ having the previous meanings,
or to the action of a heterocylic amine of formula $(III_B)$:

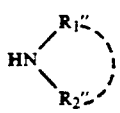

R''₁ and R''₂ having the previous meanings, so as to obtain a compound of formula ($I_{B2}$):

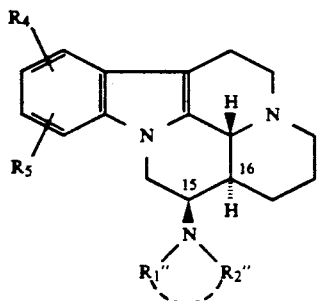

in which R''₁, R''₂, R₄ and R₅ have the meanings already indicated, and that, if desired, the compounds of formulae ($I_{A1}$) and ($I_{B1}$) are subjected to the action of a reagent which enables a radical R'₂, having the same values given previously for R₂ except for hydrogen, to be grafted on to the amine in position 15, so as to obtain the compounds of formulae ($I_{A3}$) and ($I_{B3}$):

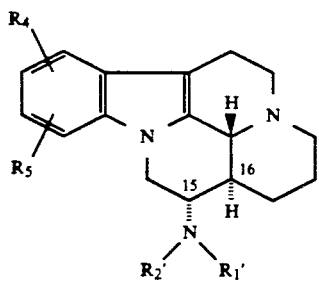

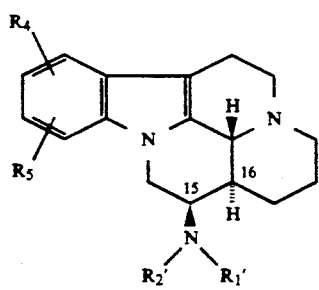

in which R'₁, R'₂, R₄ and R₅ have the previous meanings and that, if desired, when the R'₂ radical to be introduced is a methyl radical, the compounds of formulae ($I_{A1}$) and ($I_{B1}$) are subjected to the action of a formate of formula:

HCO₂R in which R is an alkyl radical containing 1 to 4 carbon atoms, so as to obtain a comound of formula (VIII):

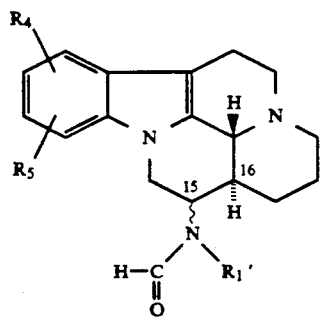

which is reduced so as to obtain compounds of formulae ($I_{A3}$) and ($I_{B3}$) in which the R'₂ radical is a methyl radical and that, if desired, the compounds of formulae ($I_{A1}$) and ($I_{B1}$) in which R'₁ is an optionally substituted arylalkyl radical are reduced, so as to obtain the compounds of formulae ($I_{A4}$) and ($I_{B4}$):

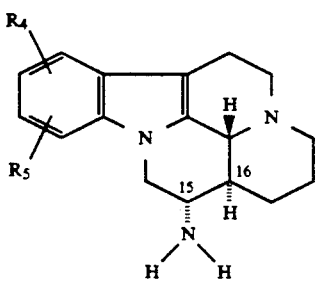

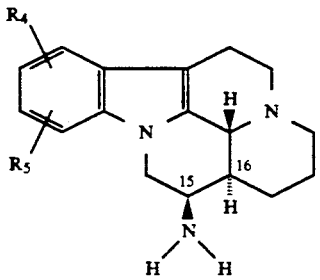

in which R₄ and R₅ have the meanings already indicated, and that if desired, the compounds of formulae ($I_{A4}$) and ($I_{B4}$) are subjected
either to the action of a reagent which enables the radicals R'₁ and R'₂ to be grafted, so as to obtain the compounds of formulae ($I_{A1}$), ($I_{B1}$), ($I_{A3}$) or ($I_{B3}$),
or to the action of an HCO₂R formate so as to obtain a compound of formula (VIII):

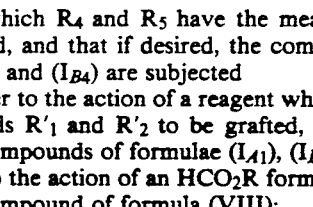

which is reduced so as to obtain a compound of formulae ($I_{A1}$) and ($I_{B1}$) in which the radical R'₁ is a methyl radical, and if desired, all the products of formula (I) thus obtained are treated with a mineral or organic acid.

In the preferred operating conditions of the process of the invention:

The reaction of the compound of formula (II) with the amines of formula (III$_A$) or (III$_B$) is carried out in the presence of a Lewis acid which is preferably titanium tetrachloride.

The reduction of the imine of formula (IV) into a compound of formula (I$_{A1}$) and of the compound of formula (V) into a compound of formula (I$_{A2}$) is carried out by sodium borohydride or by sodium cyanoborohydride.

The reduction of the imine of formula (IV) is carried out at ambient temperature and that of the compound of formula (V) at the reflux temperature of a solvent such as ethanol or acetic acid.

The reduction of the compound of formula (II) into a compound of formula (VI) is carried out by sodium borohydride in the presence of an alcohol such as methanol.

The activation of the hydroxyl function of the compound of formula (VI) is carried out by methanesulphonyl chloride.

The introduction of an R'$_2$ radical on to the amine in position 15 in the compounds of formulae (I$_{A1}$) and (I$_{B1}$) in order to obtain the compounds of formulae (I$_{A3}$) and (I$_{B3}$) is carried out with a reagent of X-R'$_2$ type in which X is a halogen atom.

When R'$_2$ is an alkyl radical, X is an iodine atom.
When R'$_2$ is a

radical, X is a chlorine atom.

In order to obtain a compound of formula (I$_{A3}$) or (I$_{B3}$) in which R'$_2$ is a methyl radical, ethyl formate is reacted with a compound of formulae (I$_{A1}$) and (I$_{B1}$) so as to obtain a compound of formula (VII) which is then reduced by a hydride. For this reduction a mixed hydride is used in particular, such as for example the mixed hydride of lithium and aluminium, the diethylhydride of sodium and aluminium. Boranedimethylamine can also be used.

The mixture of formic acid/formaldehyde can also be used as the reagent which enables the introduction of a methyl radical on to the compounds of formula (I$_{A1}$) or (I$_B^1$), or two methyl radicals on to the compounds of formula (I$_{A4}$) or (I$_{B4}$).

The method of reduction used to obtain the compounds of formulae (I$_{A4}$) and (I$_{B4}$), from compounds of formulae (I$_{A1}$) and (I$_{B1}$), is a catalytic hydrogenation, the catalyst being platinum or palladium.

The formylation of the compounds of formulae (I$_{A4}$) and (I$_{B4}$) into compounds of formula (VIII) and the reduction of compounds of formula (VIII) are carried out in the same conditions as those given above for the compounds of formulae (I$_{A1}$) and (I$_{B1}$).

In the process of the invention,

radical can be converted in the usual way into an ethyl radical by reduction with a hydride and in particular by the action of the mixed hydride of lithium and aluminium, or by the action of the dimethylsulphide borane complex.

The optically active forms of the products of formula (I) can be prepared by resolution of the racemics, according to the usual methods.

The compounds of formula (I) as defined above, as well as their addition salts with acids, present useful pharmacological properties. They present in particular a very good analgesic activity.

These properties justify their use in therapeutics and a subject of the invention is also, as medicaments, the products as defined by the formula (I) above, the said products of formula (I) being in all the possible racemic or optically active isomer forms, as well as the addition salts with pharmaceutically acceptable mineral or organic acids of the said products of formula (I).

A subject of the invention is more particularly, as medicaments:

[(±)  (15-alpha,16-alpha)]-14,15-dihydro-N-methyl-20,21-dinoreburnamenin-15-amine'

[(±)  (15-alpha,16-alpha)]-14,15-dihydro-20,21-dinoreburnamenin-15-amine,

[(±)  (15-alpha,16-alpha)]-2-[(14,15-dihydro-20,21-dinoreburnamenin-15-yl)-methylamino]-ethanol, as well as their addition salts with pharmaceutically acceptable acids.

The medicaments which are a subject of the invention can be used in the treatment of muscular, articular or nervous pains, toothache, migraines, shingles and also as a complementary treatment for infectious and feverish conditions.

The invention extends to pharmaceutical compositions containing as active principle, the medicaments defined above.

These pharmaceutical compositions can be administered by oral or rectal route, by parenteral route or by local route as a topical application on the skin and the mucosa.

These compositions can be solid or liquid and can be presented in the pharmaceutical forms currently used in human medicine, such as for example, plain or sugarcoated tablets, gelules, granules, suppositories, injectable preparations, ointments, creams, gels and aerosol preparations; they are prepared according to the usual methods. The active principle can be incorporated with the excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, and preservatives.

The usual posology, variable according to the product used, the patient being treated and the affection in question, can be, for example, from 20 mg to 2 g per day for an adult, by oral route.

The compound of formula (II) in which R$_4$ and R$_5$ represent a hydrogen atom, used as a starting product in the process of the invention, is described in European Patent No. 0,013,315.

The products of formula (II) in which at least one of the substituents R$_4$ and R$_5$ do not represent a hydrogen atom can be prepared according to the process described in the previously mentioned Patent starting from corresponding substituted tryptamines.

Another process for the preparation of products of formula (II) consists of subjecting a product of formula:

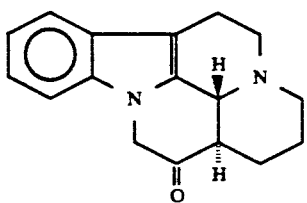

to a nitration reaction, so as to obtain a product of formula (II$_A$):

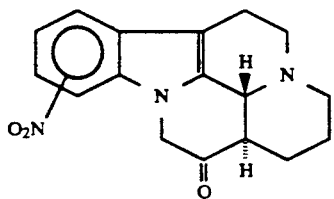

(II$_A$)

which is reduced, if appropriate, to obtain a product of formula (II$_B$):

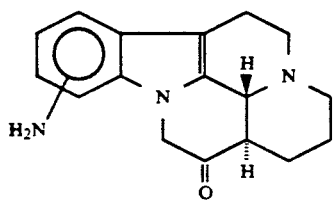

(II$_B$)

which if appropriate, either is subjected to an alkylation or acylation reaction, or is converted into a diazonium salt from which are prepared, by known processes, the derivatives of formula (II$_C$):

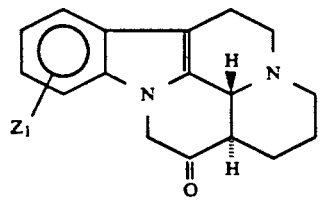

(II$_C$)

in which Z$_1$ represents a hydroxy or trifluoromethyl radical or a halogen atom, which is converted, if appropriate, into corresponding derivatives in which Z$_1$ represents an alkoxyl or alkyl radical.

Corresponding examples of the preparation of a product of formula (II) are given hereafter in the experimental part.

Finally, a subject of the present invention is, as new industrial products, in particular as intermediate products necessary for the preparation of products of formula (I), the products of formulae (IV), (V), (VI), (VII), (VIII), as well as the products of formula (II) in which R$_4$ and R$_5$ do not each represent a hydrogen atom.

The following examples illustrate the invention without however limiting it.

EXAMPLE 1

[(15-beta,16-alpha) (±)]-14,15-dihydro-N -(phenylmethyl)-20,21-dinoreburnamenin-15-amine maleate

Stage A

[(15-alpha,16-alpha) (±)]-14,15-dihydro-20,21-dinoreburnamenin-15-ol methanesulphonate 0.95 cm$^3$ of mesyl chloride is added at 20° C. to a suspension of 3.15 g of [(±) (15-alpha,16-alpha)]-14,15-dihydro-20,21-dinoreburnamenin-15-ol in 20 cm$^3$ of pyridine. The mixture is agitated for 15 hours at ambient temperature. 200 cm$^3$ of iced water is then added, followed by separating and washing with water. 4 g of expected product is obtained. M.p.=222° C.

Stage B

[(15-beta,16-alpha) (±)]-14,15-dihydro-N -(phenylmethyl)-20,21-dinoreburnamenin-15-amine A mixture of 6.8 g of product obtained as in Stage A and 100 cm$^3$ of benzylamine is agitated for 8 hours at 130° C. The solution obtained is brought to dryness. The residue is taken up in isopropyl ether. The insoluble part is filtered off and the mother liquors are concentrated to dryness. The residue is chromatographed on silica, eluting with a mixture of methylene chloride and methanol (88-2), and thus 4.36 g of expected product is recovered.

Stage C

[(15-beta,16-alpha) (±)]-14,15-dihydro-N -(phenylmethyl)-20,21-dinoreburnamenin-15-amine 0.71 g of product obtained in Stage B of Example 1 is put in solution in 40 cm$^3$ of ethanol, and a solution of 461 mg of maleic acid in 20 cm$^3$ of ethanol is added. The mixture is agitated for 3 hours at ambient temperature, then separated, washed with ethanol and then with ethyl acetate. 720 mg of expected product is obtained, M.p.=257° C.

| Analysis: for C$_{28}$H$_{31}$N$_3$O$_4$ | | | |
|---|---|---|---|
| % calculated: | C 71.01 | H 6.6 | N 8.87 |
| % found: | 70.8 | 6.5 | 8.8 |

EXAMPLE 2

[(15-beta,16-alpha) (±)]-14,15-dihydro-20,21-dinoreburnamenin-15-amine 3 g of product obtained in Stage B of Example 1 is dissolved in 150 cm$^3$ of ethanol, 600 mg of palladium at 10% on activated charcoal is added, heating to 50° C. under 200 g of hydrogen pressure and agitating for 8 hours while maintaining these conditions. The catalyst is filtered and the solution is brought to dryness. The residue is taken up in methylene chloride, the organic solution is dried with sodium sulphate, filtered and brought to dryness. The residue is chromatographed on silica (eluant: ethyl acetate - methanol—triethylamine (8-1-1).

1.5 g of expected product is obtained, M.p.=140° C.

EXAMPLE 3

[(15-beta,16-alpha) (±)]-14,15-dihydro-N-methyl-20,21-dinoreburnamenin-15-amine fumarate

Stage A

[(±) (15-beta,16-alpha)]-N-(14,15-dihydro-20,21-dinoreburnamenin-15-yl) formamide A mixture of 1.37 g of product obtained in Example 2 and 50 cm³ of ethyl formate is agitated at reflux for 5 hours. The solution obtained is brought to dryness. 1.5 g of expected product is obtained, M.p.=125° C.

Stage B

[(15-beta,16-alpha) (±)]-14,15-dihydro-N-methyl-20,21-dinoreburnamenin-15-amine

A solution of 1.5 g of product obtained in Stage A of Example 3 in 10 cm³ of tetrahydrofuran is added to a suspension of 600 mg of aluminium and lithium hydride in 20 cm³ of tetrahydrofuran. After 2 hours at ambient temperature, the mixture is heated to reflux, which is maintained for 5 hours. It is allowed to return to ambient temperature, a 10% solution of tetrahydrofuran in water is added, then extraction is carried out with ethyl acetate. After bringing to dryness, the residue is chromatographed on silica, and 720 mg of expected product is obtained, M.p.=146° C.

Stage C

[(15-beta,16-alpha) (±)]-14,15-dihydro-N-methyl-20,21-dinoreburnamenin-15-amine fumarate 680 mg of product obtained in Stage B is dissolved in 50 cm³ of ethyl acetate, and a solution of 561 mg of fumaric acid in 20 cm³ of ethanol is added under agitation. The mixture is agitated for 5 hours at ambient temperature, separated, and washed with ethyl acetate. 1.1 g of expected product is obtained, M.p.=222° C.

| Analysis: for $C_{26}H_{31}N_3O_8$ | | | |
|---|---|---|---|
| % calculated: | C 60.81 | H 6.08 | N 8.18 |
| % found: | 60.7 | 6.1 | 8.0 |

EXAMPLE 4

[(15-beta,16-alpha) (±)]-14,15-dihydro-N,N-dimethyl-20,21-dinoreburnamenin-15-amine fumarate

Stage A

[(15-beta,16-alpha) (±)]-14,15-dihydro-N,N-dimethyl-20,21-dinoreburnamenin-15-amine A solution of 1.17 g of product obtained in Example 2 in 10 cm³ of formaldehyde (at 40% in water) and 5 cm³ of formic acid is agitated at 40° C. for 2 hours 30 minutes. Then 100 cm³ of water and concentrated ammonium hydroxide is added until an alkaline pH is obtained.

Extraction is carried out with methylene chloride, and the extracts are washed with water and concentrated to dryness. The residue is chromatographed on silica (eluant: ethyl acetate—triethylamine (95-5)) and 1.12 g of expected product is obtained, M.p.=138° C.

Stage B

[(15-beta,16-alpha) (±)]-14,15-dihydro-N,N-dimethyl-20,21-dinoreburnamenin-15-amine fumarate A solution of 864 mg of fumaric acid in 50 cm³ of ethyl acetate and 10 cm³ of ethanol is added to a solution of 1.1 g of the product obtained in Stage A in 50 cm³ of ethyl acetate. The mixture is agitated for 2 hours at ambient temperature, separated and washed with ethyl acetate. 1.25 g of expected product is obtained, M.p.=215° C.

| Analysis: for $C_{23}H_9N_3O_4$ | | | |
|---|---|---|---|
| % calculated: | C 67.13 | H 7.1 | N 10.21 |
| % found: | 67.3 | 7.0 | 10.2 |

EXAMPLE 5

[(15-alpha,16-alpha) (±)]-14,15-dihydro-N-methyl-20,21-dinoreburnamenin-15-amine acid maleate

Stage A

[(15-alpha,16-alpha) (±)]-14,15-dihydro-N-methyl-20,21-dinoreburnamenin 15-amine Monomethylamine is added at −10° C., by bubbling and until saturation, to a solution of 7 g of [(±) (16-alpha)]-20,21-dinoreburnamenin-15(14H)-one in 140 cm³ of ethyl ether and 70 cm³ of toluene, then at −5° C. titanium tetrachloride is added in solution in a mixture of 10 cm³ of ether and 10 cm³ of toluene. The resulting mixture is agitated for 30 minutes at 0° C. and then for one hour at ambient temperature. The insoluble part is filtered off, washed with ether and the organic solution is brought to dryness. The residue is dissolved in 150 cm³ of ethanol and 1.5 g of sodium borohydride is added in fractions. After agitation for one hour at ambient temperature, 200 cm³ of water is added. Separating and washing with water are carried out. 6.08 g of expected product is obtained, M.p.=170° C.

Stage B

[(15-alpha,16-alpha) (±)]-14,15-dihydro-N-methyl-20,21-dinoreburnamenin-15-amine acid maleate 6.08 g of the product obtained in Stage A is dissolved in 200 cm³ of ethyl acetate; 5.01 g of maleic acid is added at 20° C. in solution in 100 cm³ of ethanol. After one hour at 25° C., the medium is separated and washed with ethyl acetate. Recrystallization is carried out from 200 cm³ of methanol.

| Analysis: for $C_{26}H_{31}N_3O_8$ | | | |
|---|---|---|---|
| % calculated: | C 60.81 | H 6.08 | N 8.18 |
| % found: | 60.6 | 6.0 | 8.1 |

EXAMPLE 6

[(15-alpha,16-alpha) (±)]-14,15-dihydro-N,N-dimethyl-20,21-dinoreburnamenin-15-amine maleate

Stage A

[(15-alpha,16-alpha) (±)]-N-(14,15-dihydro-20,21dinoreburnamenin-15-yl)-N-methyl formamide A suspension of 1.8 g of product obtained in Stage A of Example 5 and 36 cm³ of ethyl formate is agitated under reflux for 15 hours. The solution obtained is brought to dryness. 1.95 g of expected product is obtained, M.p.=216° C.

Stage B

[(15-alpha,16-alpha) (±)]-14,15-dihydro-N,N-dimethyl-20,21-dinoreburnamenin-15-amine A solution of 1.95 g of product obtained in Stage A in 50 cm³ of tetrahydrofuran is added at 0° C. to a suspension of 360 mg of lithium aluminium hydride in 10 cm³ of tetrahydrofuran. After one hour of agitation at 20° C., tetrahydrofuran at 10% in water is added. The insoluble part is filtered off and concentrated to dryness. The residue is taken up with ethyl acetate, washed with water, dried and concentrated to dryness. The residue obtained is chromatographed by eluting with ethyl acetate -triethylamine (95-5). 1.31 g of expected product is obtained, M.p.=134–135° C.

Stage C

[(15-alpha,16-alpha) (±)]-14,15-dihydro-N,N-dimethyl-20,21-dinoreburnamenin-15-amine maleate 1.03 g of maleic acid dissolved in 50 cm³ of ethanol is added to a solution of 1.31 g of product of Stage B in 100 cm³ of ethyl acetate. After 2 hours at ambient temperature, the mixture is separated and washed with ethyl acetate. 2.3 g of expected product is obtained, M.p.=172° C. By recrystallization from ethanol, 1.68 g of purified product is obtained, M.p.=175–178° C.

| Analysis: for $C_{27}H_{33}N_3O_8$ | | | |
|---|---|---|---|
| % calculated: | C 61.47 | H 6.3 | N 7.96 |
| % found: | 61.2 | 6.5 | 7.8 |

EXAMPLE 7

[(15-alpha,16-alpha) (±)]-N-(14,15-dihydro-20,21-dinoreburnamenin-15-yl)-N-methyl acetamide fumarate

Stage A

[(15-alpha,16-alpha) (±)]-N-(14,15-dihydro-20,21-dinoreburnamenin-15-yl)-N-methyl acetamide 0.2 cm³ of acetyl chloride in solution in 5 cm³ of tetrahydrofuran is added at 0° C. to a solution of 0.8 g of product obtained in Stage A of Example 5 in 0.8 cm³ of triethylamine and 15 cm³ of tetrahydrofuran. After agitation for 30 minutes at ambient temperature, the insoluble part is filtered off and brought to dryness. 750 mg of expected product is obtained, M.p.=196° C.

Stage B

[(15-alpha,16-alpha) (±)]-N-(14,15-dihydro-20,21-dinoreburnamenin-15-yl)-N-methyl acetamide fumarate A solution of 400 mg of fumaric acid in ethyl acetate is added to a solution of 750 mg of product obtained in Stage A in ethyl acetate. After 5 hours at 20° C., the mixture is separated and 920 mg of expected product is obtained, M.p.>260° C.

| Analysis: for $C_{24}H_{29}N_3O_5$ | | | |
|---|---|---|---|
| % calculated: | C 65.59 | H 6.65 | N 9.56 |
| % found: | 65.5 | 6.8 | 9.4 |

EXAMPLE

[(15-alpha,16-alpha) (±)]-14,15-dihydro-N-ethyl-N-methyl-20,21-dinoreburnamenin-15-amine maleate

Stage A

[(15-alpha,16-alpha) (±)]-14,15-dihydro-N-ethyl-N-methyl-20,21-dinoreburnamenin-15-amine 1 cm³ of borane-dimethyl sulphide complex (BH₃, Me₂S) is added to a solution of 810 mg of product obtained as in Stage A of Example 7 in 20 cm³ of tetrahydrofuran. The mixture is agitated for 2 hours under reflux. After cooling to +10° C. and adding 5 cm³ of 2N hydrochloric acid, the mixture is taken to reflux for 30 minutes.

After returning to ambient temperature, 50 cm³ of water is added and alkalization is carried out with concentrated ammonium hydroxide. After extraction with ethyl acetate, the extracts are brought to dryness and the residue obtained is chromatographed on silica (eluant: methylene chloride—methanol (97-3). 690 mg of expected product is obtained, M.p.=100° C.

Stage B

[(15-alpha,16-alpha) (±)]-14,15-dihydro-N-ethyl-N-methyl-20,21-dinoreburnamenin-15-amine maleate A solution of 518 mg of maleic acid in 30 cm³ of ethanol is added at 20° to a solution of 690 mg of product obtained in Stage A. After 2 hours of agitation at 20° C., the mixture is separated, washed with ethanol and 1.03 g of expected product is obtained. M.p.=192°.

| Analysis: for $C_{28}H_{35}N_3O_8$ | | | |
|---|---|---|---|
| % calculated: | C 62.09 | H 6.51 | N 7.76 |
| % found: | 62.0 | 6.7 | 7.7 |

EXAMPLE 9

[(15-alpha,16-alpha) (±)]-3,4-dichloro-N-(14,15-dihydro-20,21-dinoreburnamenin-15-yl)-N-methyl benzeneacetamide fumarate

Stage A

[(15-alpha,16-alpha) (±)]-3,4-dichloro-N-(14,15-dihydro-20,21-dinoreburnamenin-15-yl)-N-methyl benzeneacetamide 1 g of 3,4-dichloro phenylacetic acid chloride in solution in 2 cm³ of tetrahydrofuran is added to a solution of 800 mg of product obtained as in Stage A of Example 5 in 25 cm³ of tetrahydrofuran and 0.8 cm³ of triethylamine. After agitation for one hour, the insoluble part is filtered off, and the organic solution is brought to dryness. The residue is chromatographed on silica (eluant: methylene chloride—methanol (95-5)); after it has been brought to dryness, the residue is made into a paste in 50 cm³ of isopropyl ether, and one obtains 1 g of expected product. M.p.=166° C.

Stage B

[(15-alpha,16-alpha)
(±)]-3,4-dichloro-N-(14,15-dihydro-20,21-dinoreburnamenin-15-yl)-N-methyl benzeneacetamide fumarate 1 g of product obtained in Stage A is dissolved in a mixture of 10 cm³ of ethanol and 50 cm³ of ethyl acetate. 248 mg of fumaric acid dissolved in 20 cm³ of ethanol is added to this solution. Agitation is carried out for 4 hours at ambient temperature, followed by separation and washing with ethanol and then with ethyl acetate. 970 mg of expected product is obtained. M.p.=257° C.

| Analysis: for $C_{30}H_{31}N_3O_5Cl_2$ | | | | |
|---|---|---|---|---|
| % calculated: | C 61.65 | H 5.34 | N 7.19 | Cl 12.13 |
| % found: | 61.7 | 5.5 | 6.9 | 11.8 |

EXAMPLE 10

[(15-alpha,16-alpha)
(±)]-14,15-dihydro-15-(1-pyrrolidinyl)-20,21-dinoreburnamenine maleate

Stage A

[(16-alpha)
(±)]-15-(1-pyrrolidinyl)-20,21-dinoreburnamenine 0.72 cm³ of titanium tetrachloride in solution in a mixture of 20 cm³ of ethyl ether and 20 cm³ of toluene is added at 0° C. to a solution of 3 g of [(16-alpha) (±)]-20,21-dinoreburnamenin-15(14H)-one in a mixture of 150 cm³ of ethyl ether and 150 cm³ of toluene. The resultant mixture is agitated at 0° C. for 30 minutes then for 15 hours at ambient temperature. The insoluble part is filtered off and brought to dryness. 3.5 g of expected product is obtained. M.p.=180° C.

Stage B [(15-alpha,16-alpha)
(±)]-14,15-dihydro-15-(1-pyrrolidinyl)-20,21-dinoreburnamenine 2.08 g of sodium borohydride is added in fractions to a solution of 3.5 g of product obtained in Stage A in 200 cm³ of ethanol, then the whole is heated under reflux, which is maintained for 4 hours.

The mixture is left to return to ambient temperature and 200 cm³ of ice-cooled water is added, the precipitate is separated off and washed with water. The crude product obtained is chromatographed on silica (eluant: methylene chloride—methanol (95-5)) then the dry extract is recrystallized from 180 cm³ of isopropyl ether. 1.7 g of expected product is obtained. M.p.=156° C.

Stage C

[(15-alpha,16-alpha)
(±)]-14,15-dihydro-15-(1-pyrrolidinyl)-20,21-dinoreburnamenine maleate A solution of 1.23 g of maleic acid in 50 cm³ of ethanol is added to a solution of 1.7 g of product obtained in Stage B in a mixture of 50 cm³ of ethyl acetate and 50 cm³ of ethanol. Agitation is carried out for 15 hours at ambient temperature, followed by separation and washing with ethyl acetate.

2.6 g of expected product is obtained. M.p.=232° C.

| Analysis: for $C_{29}H_{35}N_3O_8$ | | | |
|---|---|---|---|
| % calculated: | C 62.92 | H 6.37 | N 7.59 |
| % found: | 63.2 | 6.5 | 7.4 |

EXAMPLE 11

[(15-alpha,16-alpha) (±)]-14,15-dihydro-15-(4-morpholinyl)-20,21-dinoreburnamenine maleate

Stage A

[(16-alpha)
(±)]-15-(4-morpholinyl)-20,21-dinoreburnamenine 3.6 cm³ of morpholine is added to a solution of 2.13 g of [(16-alpha) (±)]-20,21-dinoreburnamenin-15(14H)-one in a mixture of 40 cm³ of ether and 40 cm³ of toluene. The resultant mixture is cooled to −5° C., then 0.5 cm³ of titanium chloride in solution in a mixture of 10 cm³ of ethyl ether and 10 cm³ of toluene is added without exceeding 0° C. Agitation is carried out for one hour at 0° C., then for 15 hours at ambient temperature. The insoluble part is filtered off and the organic solution is concentrated to dryness. 1.6 g of expected product is obtained. M.p.=176° C.

Stage B

[(15-alpha,16-alpha)
(±)]-14,15-dihydro-15-(4-morpholinyl)-20,21-dinoreburnamenine 2 g of sodium borohydride is added to a solution, heated to 60° C., of 1.6 g of product obtained in Stage A in 50 cm³ of acetic acid, the whole is agitated for 20 minutes at 60° C. then left to return to ambient temperature. 200 cm³ of water is added and the medium is alkalized with concentrated ammonium hydroxide. The precipitate formed is separated and washed with water. The crude product is purified by chromatography on silica (eluant: ethyl acetate with 1% triethylamine). 1.25 g of expected product is obtained. M.p.=222° C.

Stage C

[(15-alpha,16-alpha)
(±)]-14,15-dihydro-15-(4-morpholinyl)-20,21-dinoreburnamenine maleate 1 g of the base obtained in Stage B is dissolved in a mixture of 100 cm³ of ethyl acetate and 50 cm³ of ethanol, and a solution of 692 mg of maleic acid in 20 cm³ of ethanol is added at 20o. Agitation is carried out for two and a half hours at 20° C., then for 30 minutes at 0° C. Separation is done, followed by washing with ethyl acetate. 1.07 g of expected product is obtained. M.p.=250° C.

| Analysis: for $C_{25}H_{31}N_3O_5$ | | | |
|---|---|---|---|
| % calculated: | C 66.21 | H 6.89 | N 9.26 |
| % found: | 66.5 | 6.9 | 9.2 |

EXAMPLE 12

[(15-alpha,16-alpha) (±)]-14,15-dihydro-N-(2-phenyl ethyl)-20,21-dinoreburnamenin-15-amine maleate

Stage A

[(15-alpha,16-alpha) (±)]-14,15-dihydro-N-(2-phenylethyl)-20,21-dinoreburnamenin-15-amine 3.8 cm³ of phenethylamine is added to a solution of 1.6 g of [(16-alpha) (±)]-20,21-dinoreburnamenin-15(14H)-one in a mixture of 60 cm³ of ether and 60 cm³ of toluene. The resultant mixture is cooled to 0° C. +5° C. and 0.4 cm³ of titanium tetrachloride in solution in a mixture of 10 cm³ of ether and 10 cm³ of toluene is added. Agitation is carried out for 30 minutes at 0° C., then for 2 hours at ambient temperature. The insoluble part is filtered off, followed by concentration to dryness. The residue is dissolved in 75 cm³ of ethanol and 912 mg of sodium borohydride is added at ambient temperature. Next, 100 cm³ of ice-cooled water is added, then extraction is done with ethyl acetate and the extracts are concentrated to dryness. The residue is chromatographed on silica (eluant: methylene chloride—methanol (95–5)). 1.2 g of expected product is obtained. M.p.=127° C.

Stage B

[(15-alpha,16-alpha) (±)]-14,15-dihydro-N-(2-phenyl ethyl)-20,21-dinoreburnamenin-15-amine maleate 1.07 g of the product obtained in Stage A is dissolved in 100 cm³ of ethyl acetate and 668 mg of maleic acid in solution in 50 cm³ of ethanol is added to this solution. After 5 hours in contact, separation is carried out, followed by washing with ethyl acetate, and 1.3 g of expected product is obtained. M.p.=235° C.

| Analysis: for $C_{33}H_{37}N_3O_8$ | | | |
|---|---|---|---|
| % calculated: | C 65.66 | H 6.18 | N 6.96 |
| % found: | 65.6 | 6.3 | 6.8 |

EXAMPLE 13

[(15-alpha,16-alpha) (±)]-14,15-dihydro-15-(4-phenyl-1-piperazinyl)-20,21-dinoreburnamenine acid oxalate

Stage A (16-alpha) (±) 15-(4-phenyl-1-piperazinyl)-20,21-dinoreburnamenine

The operation is carried out as in Stage A of Example 11 using 533 mg of [(16-alpha) (±)]-20,21-dinoreburnamenine -15(14H)-one and 1.5 cm³ of N-phenylpiperazine. After purification by trituration in hexane, 610 mg of expected product is obtained. M.p.=202° C.

Stage B

[(15-alpha,16-alpha) (±)]-14,15-dihydro-15-(4-phenyl-1-piperazinyl)-20,21-dinoreburnamenine The operation is carried out as in Stage B of Example 11 using 3.8 g of product prepared as in Stage A. After chromatography on silica (eluant: ethyl acetate), 1.8 g of expected product is obtained. M.p.=120° C.

Stage C

[(15-alpha,16-alpha) (±)]-14,15-dihydro-15-(4-phenyl-1-piperazinyl)-20,21-dinoreburnamenine acid oxalate 1.03 g of product obtained in Stage B is dissolved in 50 cm³ of ethyl acetate and 553 mg of oxalic acid dissolved hot in 50 cm³ of ethyl acetate is added. Agitation is carried out for 3 hours at ambient temperature, then for 15 minutes at 0° C. After separation and drying under reduced pressure, 1.15 g of expected product is collected. M.p.>260° C.

| Analysis: $C_{29}H_{34}N_4O_4$ | | | |
|---|---|---|---|
| Calculated: | C % 69.3 | H % 6.82 | N % 11.15 |
| Found: | 69.4 | 6.8 | 11.0 |

EXAMPLE 14

[(15-alpha,16-alpha) (±)]-14,15-dihydro-15-(4-methyl-1-piperazinyl)-20,21-dinoreburnamenine acid oxalate

Stage A

[(16-alpha) (±)]-15-(4-methyl-1-piperazinyl)-20,21-dinoreburnamenine

The operation is carried out as in Stage A of Example 11 using 3 g of [(16-alpha) (±)]-20,21-dinoreburnamenin -15(14H)-one and 5.6 cm³ of N-methylpiperazine. 3.9 g of expected product is obtained, used as it is for the following stage.

Stage B [(15-alpha,16-alpha) (±)]-14,15-dihydro-15-(4-methyl-1-piperazinyl)-20,21-dinoreburnamenine The operation is carried out as in Stage B of Example 11 using 3 g of product obtained in Stage A and 1.5 g of sodium cyano borohydride. After chromatography on silica (eluant: ethyl acetate—methanol—triethylamine 95–5–5), 1.86 g of expected product is obtained.

Stage C

[(15-alpha,16-alpha) (±)]-14,15-dihydro-15-(4-methyl-1-piperazinyl)-20,21-dinoreburnamenine acid oxalate The operation is carried out as in Stage C of Example 11 using 1 g of the base obtained in Stage B and 771 mg of oxalic acid. 1.45 g of expected product is obtained. M.p.>260° C.

| Analysis: $C_{26}H_{34}N_4O_8$ | | | |
|---|---|---|---|
| Calculated: | C % 58.86 | H % 6.46 | N % 10.56 |
| Found: | 59.1 | 6.5 | 10.5 |

EXAMPLE 15

[(15-alpha,16-alpha) (±)]-14,15-dihydro-20,21-dinoreburnamenin-15-amine maleate

Stage A

[(15-alpha,16-alpha) (±)]-14,15-dihydro-N-(phenylmethyl) -20,21-dinoreburnamenin-15-amine The operation is carried out as in Stage A of Example 12 using 2.13 g of [(16-alpha) (±)]-20,21-dinoreburnamenin -15(14H)-one, 4.4 cm$^3$ of benzylamine and 0.5 cm$^3$ of titanium tetrachloride. After extraction with ethyl acetate and concentration to dryness, the residue is taken up in isopropyl ether, separated and dried under reduced pressure at 50° C. 2.07 g of expected product is recovered. M.p.=166° C.

Stage B

[(15-alpha,16-alpha) (±)]-14,15-dihydro-20,21-dinoreburnamenin-15-amine 1.5 g of product obtained in Stage A is hydrogenated for 6 hours at 50° C. in 100 cm$^3$ of ethanol in the presence of 300 mg of activated charcoal with 10% of palladium. The catalyst is filtered off, the organic solution is concentrated to dryness and 1.03 g of expected product is recovered. M.p.=160° C.

Stage C

[(15-alpha,16-alpha) (±)]-14,15-dihydro-20,21-dinoreburnamenin-15-amine maleate 1.18 g of the base obtained in Stage B is dissolved in 50 cm$^3$ of ethanol and 100 cm$^3$ of ethyl acetate and 1.02 g of maleic acid dissolved previously in 50 cm$^3$ of ethanol is added. Agitation is carried out for 3 hours, the precipitate is separated off, washed with ethanol, dried at 50° under reduced pressure, and after recrystallization from ethanol, 1.2 g of expected product is collected. M.p.=230° C.

| Analysis: C$_{25}$H$_{29}$N$_3$O$_8$ | | | |
|---|---|---|---|
| Calculated: | C % 60.11 | H % 5.85 | N % 8.41 |
| Found: | 60.2 | 5.6 | 8.4 |

EXAMPLE 16

[(15-alpha,16-alpha) (±)]-2-[(14,15-dihydro -20,21-dinoreburnamenin-15-yl)-methylamino]-ethanol fumarate

Stage A

Ethyl [(15-alpha,16-alpha) (±)]-[14,15-dihydro -20,21-dinoreburnamenin-15-yl)-methylamino]-acetate 2 g of [(15-alpha,16-alpha) (±)]-14,15-dihydro -N-methyl-20,21-dinoreburnamenin-15-amine is dissolved, under an inert atmosphere, in a mixture containing 3 cm$^3$ of triethylamine and 100 cm$^3$ of tetrahydrofuran, and 0.83 cm$^3$ of ethyl iodo acetate is added, and once again after 2 hours, then 7 hours of agitation, an additional 0.83 cm$^3$ of ethyl iodo acetate is added. The resultant mixture is maintained under agitation for a further 8 hours, filtered, and the organic phase is concentrated to dryness; the residue is chromatographed on silica (eluant: methylene chloride—methanol 95-5) and 1.8 g of expected product is collected.

Stage B

[(15-alpha,16-alpha) (±)]-2-[(14,15-dihydro-20,21-dinoreburnamenin-15-yl)-methylamino]-ethanol 1.8 cm$^3$ of borane-disulphone complex is added, under an inert atmosphere, to 1.8 g of product obtained in Stage A in solution in 50 cm$^3$ of tetrahydrofuran, then the mixture is heated under reflux for one hour 30 minutes. It is left to return to ambient temperature, 50 cm$^3$ of 0.1N hydrochloric acid is added, with agitation for 15 minutes at 40° C.; 100 cm$^3$ of ice-cooled water is added, and alkalization is carried out with ammonium hydroxide. The precipitate is separated off, washed with water, dried at 80° C. under reduced pressure and 0.8 g of expected product is obtained after purification by triturating in acetone. M.p.=200° C.

Stage C

[(15-alpha,16-alpha) (±)]-2-[(14,15-dihydro-20,21-dinoreburnamenin-15-yl)-methylamino]-ethanol fumarate 457 mg of the base obtained in Stage B is dissolved in 100 cm$^3$ of ethyl acetate and 10 cm$^3$ of ethanol, and 326 mg of fumaric acid dissolved in 10 cm$^3$ of ethanol is added. Agitation is carried out for 2 hours at 0° C., followed by separation and drying under reduced pressure at 70° C. 460 mg of expected product is obtained. M.p.=208° C.

| Analysis: C$_{29}$H$_{31}$N$_3$O$_5$ | | | |
|---|---|---|---|
| Calculated: | C % 65.29 | H % 7.07 | N % 9.52 |
| Found: | 65.3 | 7.1 | 9.6 |

EXAMPLE 17

[(3-alpha,15-beta)-14,15-dihydro-20 21-dinoreournamenin-15-amine acid maleate

Stage A

[3-alpha,15-beta (S)]-14,15-dihydro-N-(1-phenylethyl)-20,21-dinoreburnamenin-15-amine and the corresponding [15-alpha (S) 16-alpha]isomer 4.1 cm$^3$ of L(-) alpha-phenethylam.ine is added to a suspension of 2.13 g of [(16-alpha (±)]-20,21-dinoreburnamenin-15(14H)-one in suspension in 50 cm$^3$ of ether and 50 cm$^3$ of toluene The resultant mixture is cooled to 0° C./+5° C. and 0.5 cm$^3$ of titanium tetrachloride in solution in a mixture of 10 cm$^3$ of ether and 10 cm$^3$ of toluene is added. Agitation is carried out for 30 minutes at 0° C., then for one hour at ambient temperature. 75 cm$^3$ of ethanol is added, and 1.5 g of sodium borohydride is added at ambient temperature, followed by agitation for one hour 30 minutes at ambient temperature. Next 200 cm$^3$ of ice-cooled water is added and extraction is carried out with ethyl acetate, and the extracts are concentrated to dryness. The residue is chromatographed on silica (eluant: methylene chloride—methanol 95-5). 790 mg of isomer A (3-alpha isomer) is obtained, M.p.=166° C.

[alpha$_D$]=+53.5°±1.5° (c=1% CHCl$_3$) and 460 mg of isomer B (16-alpha isomer) is obtained, M.p.=182° C.,

[alpha$_D$]=206°±3° (c=1% CHCl$_3$).

Stage B

[(3-alpha,15-beta)]-14,15-dihydro-20,21-dinoreburnamenin-15-amine 500 mg of isomer A prepared in Stage A in solution in 20 cm$^3$ of ethanol is hydrogenated for 16 hours at 60° C. under a pressure of 500 g, in the presence of 100 mg of activated charcoal with 10% palladium. The catalyst is filtered off, the organic phase is evaporated to dryness, the residue is chromatographed on silica (eluant: ethyl acetate—triethylamine—methanol 8-1-1) and 290 mg of expected product is collected. M.p.=135° C.

[alpha$_D$]=−29°±2° (c=0.5% ethanol).

Stage C

[(3-alpha,15-beta)-14,15-dihydro-20,21-dinoreburnamenin-15-amine acid maleate 0.8 g of product prepared as in Stage B is dissolved in 50 cm$^3$ of ethyl acetate and 50 cm$^3$ of ethanol and 694 mg of maleic acid dissolved in 50 cm$^3$ of ethanol is added. Agitation is carried out for 2 hours at ambient temperature, the precipitate is separated off and dried at 80° C. under reduced pressure. 1.2 g of expected product is recovered. M.p.=240° C.

| Analysis: C$_{17}$H$_{21}$N$_3$. 2 C$_4$H$_4$O$_4$ | | | |
|---|---|---|---|
| Calculated: | C % 60.11 | H % 5.85 | N % 8.41 |
| Found: | 60.1 | 5.8 | 8.1 |

EXAMPLE 18

[(15-alpha,16-alpha)]-14,15-dihydro-20,21-dinoreburnamenin-15-amine acid maleate

Stage A

[(15-alpha,16-alpha]-14,15-dihydro-20,21-dinoreburnamenin-15-amine

The operation is carried out as in Stage B of Example 17 using at the start 3.1 g of isomer B prepared as in Stage A of Example 17. 1.15 g of expected product is obtained. M.p.=135° C.

[alpha$_D$]=+25°±2° (c=0.5% ethanol).

Stage B

[(15-alpha,16-alpha)]-14,15-dihydro-20,21-dinoreburnamenin-15-amine acid maleate The operation is carried out as in Stage C of Example 17 using 550 mg of product prepared in Stage A and 477 mg of maleic acid. 940 mg of expected product is obtained. M.p.=238° C.

| Analysis: C$_{17}$H$_{21}$N$_3$. 2 C$_4$H$_4$O$_4$ | | | |
|---|---|---|---|
| Calculated: | C % 60.11 | H % 5.85 | N % 8.41 |
| Found: | 59.9 | 5.7 | 8.5 |

EXAMPLE 19

[(3-alpha,15-beta)]-14,15-dihydro-N-methyl-20,21-dinoreburnamenin-15-amine acid maleate

Stage A

[(3-alpha,15-beta)]-N-[14,15-dihydro-20,21-dinoreburnamenin-15-yl]-formamide 1 g of the base obtained in Stage B of Example 17 in solution in a mixture containing 30 cm$^3$ of ethyl formate and 30 cm$^3$ of tetrahydrofuran is heated under reflux for 6 hours. After filtering and concentrating to dryness, 1.13 g of expected product is obtained. M.p.=211° C.

[alpha$_D$]=+53° (c=1% CHCl$_3$).

Stage B

[(3-alpha,15-beta)]-14,15-dihydro-N-methyl-20,21-dinoreburnamenine-15-amine 1.1 g of product obtained in Stage A is dissolved in 50 cm$^3$ of tetrahydrofuran, then 1.1 cm$^3$ of borane-disulphide complex is added slowly and the whole is heated under reflux for one hour 30 minutes. It is left to return to ambient temperature then acidified using 0.1N hydrochloric acid. Agitation is carried out for 15 hours at ambient temperature, followed by alkalization by the addition of ammonium hydroxide and extraction with ethyl acetate. The organic phase is washed with water, dried and concentrated to dryness, and the residue is chromatographed on silica (eluant: ethyl acetate—triethylamine—methanol 8-1-1). 70 mg of expected product is obtained. M.p.=138° C.

[alpha$_D$]=+9.5°±1° (c=1% CHCl$_3$).

Stage C

[(3-alpha,15-beta)]-14,15-dihydro-N-methyl-20,21-dinoreburnamenine-15-amine acid maleate 690 mg of base obtained as in Stage B is dissolved in 100 cm$^3$ of hot ethyl acetate, 567 mg of maleic acid in solution in a mixture containing 50 cm$^3$ of ethyl acetate and 10 cm$^3$ of ethanol is added, with agitation for 2 hours at ambient temperature, then for 30 minutes at 0° C. The precipitate is separated off, washed with ethyl acetate and dried at 60° C. under reduced pressure. 1.06 g of expected product is collected. M.p.=165° C.

| Analysis: C$_{18}$H$_{23}$N$_3$. 2 C$_4$H$_4$O$_4$ | | | |
|---|---|---|---|
| Calculated: | C % 60.81 | H % 6.08 | N % 8.18 |
| Found: | 60.6 | 6.2 | 8.1 |

EXAMPLE 20

[(15-alpha,16-alpha)]-N-methyl-20,21-dinoreburnamenin-15-amine acid maleate

Stage A

[15-alpha,16-alpha]-N-[14,15-dihydro-20,21-dinoreburnamenin-15-yl]-formamide

The operation is carried out as in Stage A of Example 19 using 560 mg of the base obtained in Stage A of Example 18 and 10 cm$^3$ of ethyl formate. The product obtained is chromatographed on silica (eluant: ethyl acetate—triethylamine—methanol 8-1-1). 522 mg of expected product is obtained. M.p.=210° C.

[alpha$_D$]=−57.5°±1.5° (c=1% CHCl$_3$).

Stage B

[(15-alpha,16-alpha)]-N-methyl-20,21-dinoreburnamenin-15-amine

The operation is carried out as in Stage B of Example 19 using 490 mg of the product obtained in Stage A and 0.5 cm³ of borane-disulphide complex. After chromatography on silica (eluant: methylene chloride—methanol—ammonium hydroxide 93-6.5-0.5), 220 mg of expected product is obtained. M.p.=135° C.

Stage C

[(15-alpha,16-alpha)]-N-methyl-20,21-dinoreburnamenin-15-amine acid maleate

The operation is carried out as in Stage C of Example 15 using 524 mg of base prepared as in Stage B and 432 mg of maleic acid. 750 mg of product is obtained which is purified by recrystallization from ethanol and 660 mg of expected product is collected. M.p.=170° C.

| Analysis: $C_{18}H_{23}N_3$, 2 $C_4H_4O_4$ | | | |
|---|---|---|---|
| Calculated: | C % 60.81 | H % 6.08 | N % 8.18 |
| Found: | 60.8 | 6.2 | 8.1 |

EXAMPLE 21

[(15-alpha,16-alpha) (±)]-14,15-dihydro-N-methyl-9-nitro-20,21-dinoreburnamenin-15-amine neutral maleate

Stage A

[(15-alpha,16-alpha) (±)]-14,15-dihydro-N-methyl-9-nitro-20,21-dinoreburnamenin-15-amine 1.5 g of (16-alpha) (±) 9-nitro-20,21-dinoreburnamenin-15(14H)-one in suspension in a mixture containing 100 cm³ of ether and 100 cm³ of toluene is cooled to 0° C. and monomethylamine is bubbled through until saturation is achieved. 0.35 cm³ of titanium tetrachloride in solution in a mixture containing 5 cm³ of ether and 5 cm³ of toluene is added slowly at 0° C., then agitated for one hour 30 minutes at 20° C. 100 cm³ of ethanol and 535 mg of sodium borohydride are added, with agitation for 2 hours, then 300 cm³ of ice-cooled water is added, and extraction is done with ethyl acetate. The organic phase is washed with water, dried and concentrated to dryness and the residue is chromatographed on silica (eluant: ethyl acetate—methanol—triethylamine 8-1-1). 1 g of expected product is obtained. M.p.=168° C.

Stage B

[(15-alpha,16-alpha) (±)]-14,15-dihydro-N-methyl-9-nitro-20,21-dinoreburnamenin-15-amine neutral maleate The operation is carried out as in Stage C of Example 15 using 930 mg of the base prepared in Stage B and 661 mg of maleic acid. 1.12 g of expected product is obtained.

M.p.>260° C.

| Analysis: $C_{18}H_{22}N_4O_2$, $C_4H_4O_4$ | | | |
|---|---|---|---|
| Calculated: | C % 59.71 | H % 5.92 | N % 12.66 |
| Found: | 59.6 | 5.9 | 12.6 |

Preparation of the [(16-alpha) (±)]-9-nitro-20,21-dinoreburnamenin-15(14H)-one and the corresponding 11-nitro derivative 5 cm³ of nitric acid is mixed at −25° C. with 300 cm³ of chloroform and 75 cm³ of acetic acid, then 15 g of [(16-alpha) (±)]-20,21-dinoreburnamenin-15(14H)-one in solution in 100 cm³ of chloroform is added drop by drop. The whole is maintained under agitation for 30 minutes, the reaction mixture is poured into 500 cm³ of ice-cooled water then alkalized using concentrated ammonium hydroxide. The organic phase is separated off, washed with water, dried and concentrated to dryness. The residue is chromatographed on silica (eluant: ethyl acetate) and 5.3 g of 9-nitro derivative is obtained, M.p. 230° C., and 5.62 g of 11-nitro derivative is obtained, M.p.=250° C.

EXAMPLE 22

[(15-alpha,16-alpha) (±)]-14,15-dihydro-N-methyl-11-nitro-20,21-dinoreburnamenin-15-amine neutral maleate

Stage A

[(15-alpha,16-alpha) (±)]-14,15-dihydro-N-methyl-11-nitro-20,21-dinoreburnamenin-15-amine The operation is carried out as in Stage A of Example 21 using 1.5 g of 11-nitro derivative obtained as indicated in the above preparation. 1 g of expected product is obtained. M.p.=168° C.

Stage B

[(15-alpha,16-alpha) (±)]-14,15-dihydro-N-methyl-11-nitro-20,21-dinoreburnamenin-15-amine neutral maleate The operation is carried out as in Stage C of Example 15 using 930 mg of the base prepared in Stage A. 1.12 g of expected product is obtained. M.p.>260° C.

| Analysis: $C_{18}H_{22}N_4O_2$, $C_4H_4O_4$ | | | |
|---|---|---|---|
| Calculated: | C % 59.71 | H % 5.92 | N % 12.66 |
| Found: | 59.6 | 5.9 | 12.6 |

EXAMPLE 23

Tablets were prepared corresponding to the following formula:

| Product of Example 5 | 50 mg |
|---|---|
| Excipient q.s. for | 350 mg |

(Detail of excipient: lactose, talc, starch, magnesium stearate).

ANALGESIC ACTIVITY

1) Hot-plate test

Females mice weighing 22 to 24 g are placed one by one on a copper plate maintained at 56° C.: the reaction to the pain is shown by the licking of the animal's front paws; this reaction time is noted and only the mice reacting under 8 seconds are retained.

The animals are divided into equal groups and treated with the product to be studied, administered by oral group, one group receiving only the vehicle. The reaction time to the pain is again measured 30 minutes after the treatment. The active dose or $AD_{100}$ is the dose which increases the reaction time by 100%, 30 minutes after the treatment, taking into account the variations in the reaction times of the control animals.

For the product of Example 5 the $AD_{100}$ is 100 mg/kg.

2) Test for stretching with acetic acid

The test used is based on the fact pointed out by R. KOSTER and Coll., (Fed., Proc., 1959, 1B, 412) according to which the intraperitoneal injection of acetic acid causes, in a mouse, repeated stretching and twisting movements which can persist for more than 6 hours. The analgesics prevent or diminish this syndrome which can be considered as the externalization of a widespread abdominal pain. A solution of 1% acetic acid in water is used. The dose which releases the syndrome is in these conditions 0.01 cm³/g, that is 100 mg/kg of acetic acid.

The product studied is administered by buccal route half an hour before the injection of acetic acid, the mice having gone without food since the day before the experiment.

The stretchings are observed and counted for each mouse, for an observation period of 15 minutes commencing 5 minutes after the injection of acetic acid.

The results are expressed in $AD_{50}$, that is the dose which enables a decrease of 50% in the number of stretchings relative to the control animals to be obtained.

The $AD_{50}$ of the product of Example 5 is 70 mg/kg.

We claim:

1. A compound selected from the group consisting of a compound of the formula (I):

in which $R_1$ and $R_2$ are individually selected from the group consisting of hydrogen, an alkyl of 1 to 5 carbon atoms, $-(CH_2)_n-OH$ in which n is between 2 and 5, an aryl or arylalkyl of 7 to 12 carbon atoms, these two radicals being optionally substituted, $$-\underset{\underset{O}{\|}}{C}-R_3$$

in which $R_3$ is an alkyl of 7 to 12 carbon atoms, these two radicals being optionally substituted, with the proviso that $R_1$ and $R_2$ are not both aryl simultaneously, or $R_1$ and $R_2$ form, together with the nitrogen atom to which they are linked, a saturated or unsaturated heterocyclic which can contain a second heteroatom chosen from oxygen, sulphur and nitrogen optionally substituted by an alkyl of 1 to 5 carbon atoms, aryl, arylalkyl of 7 to 12 carbon atoms, these radicals being optionally substituted, $R_4$ and $R_5$ are individually selected from the group consisting of hydrogen, halogen, alkyl or alkoxy of 1 to 5 carbon atoms, hydroxy, trifluoromethyl or nitro, the said products of formula (I) being in all the possible enantiomeric and diastereoisomeric forms and its non-toxic, pharmaceutically acceptable acid addition salts.

2. Compounds of formula (I), as defined in claim 1, characterized in that $R_1$ and $R_2$, identical or different, represent a hydrogen atom, a methyl or ethyl radical, a $$-\underset{\underset{O}{\|}}{C}-R_3$$

radical in which $R_3$ is a methyl or ethyl, phenyl or benzyl radical optionally substituted by one or more chlorine atoms, a $-CH_2-CH_2-OH$ radical or $R_1$ and $R_2$ form together with the nitrogen atom a pyrrolidinyl, morphol-inyl or piperazinyl radical, the nitrogen atom of which is substituted by a methyl or phenyl radical, $R_4$ and $R_5$ represent a hydrogen atom or $R_4$ represents a nitro radical in position 9 or 11 and $R_5$ represents a hydrogen atom, and their addition salts with acids.

3. A compound of claim 1 which is [(±) (15-alpha,16-alpha)]-14,15-dihydro-N-methyl-20,21-dinoreburn-amenin-15-amine and its addition salts with acids.

4. A compound of claim 1 which is [(±) (15-alpha,16-alpha)]-14,15-dihydro-20,21-dinoreburnamenin-15-amine and its addition salts with acids.

5. A compound of claim 1 which is [(±) (15-alpha,-6-alpha)]-2-[(14,15-dihydro-20,21-dinoreburnamenin-15-yl)-methylamino]-ethanol and its addition salts with acids.

6. A method of reducing pain in warm-blooded animals comprising administering to warm-blooded animals an analgesically effective amount of at least one compound of claim 1.

7. An analgesic composition comprising an analgesically effective amount of a compound of claim 1 and an inert pharmaceutical carrier.

8. A composition of claim 7 wherein $R_1$ and $R_2$ are individually selected from the group consisting of hydrogen, methyl, ethyl, $-CH_2-CH_2OH$ and $$-\underset{\underset{}{}}{\overset{\overset{O}{\|}}{C}}R_3,$$

or together with the nitrogen atom to which they are attached form a heterocycle selected from the group consisting of pyrolidinyl, morpholino and piperazinyl optionally substituted on the nitrogen with methyl or phenyl, $R_3$ is selected from the group consisting of methyl, ethyl, phenyl and benzyl optionally substituted with at least one chlorine, $R_4$ and $R_5$ are both hydrogen or $R_4$ is $-NO_2$ in the 9- or 11- position and $R_5$ is hydrogen.

9. A composition of claim 7 wherein the active compound is [(±)(15α, 16α)]-14,15-dihydro-N-methyl-20,21-dinoreburn-amenin-15-amine or its non-toxic pharmaceutically acceptable acid addition salts.

10. A composition of claim 7 wherein the active compound is [(±)(15α, 16α)]-14,15-dihydro-20,21-dinoreburnamenin -15-amine or its non-toxic pharmaceutically acceptable acid addition salts.

11. The method of claim 6 wherein the compound is [(±)(15α, 16α)]-14,15-dihydro-N-methyl-20,21-dinoreburnamenin -15-amine.

* * * * *